United States Patent [19]
Thompson et al.

[11] Patent Number: 5,571,791
[45] Date of Patent: Nov. 5, 1996

[54] MODIFIED POLYPEPTIDE FRAGMENTS OF THE GLUCOCORTICOID RECEPTOR

[75] Inventors: E. Brad Thompson; Lynne V. Nazareth, both of Galveston, Tex.

[73] Assignee: Board of Regents, The University of Texas System, Austin, Tex.

[21] Appl. No.: 561,072

[22] Filed: Nov. 20, 1995

Related U.S. Application Data

[62] Division of Ser. No. 87,151, Jul. 2, 1993, Pat. No. 5,468,624.

[51] Int. Cl.$^6$ ............................ A61K 38/00; C07K 14/00
[52] U.S. Cl. ............................ 514/12; 530/300; 435/69.1
[58] Field of Search ........................ 435/69.1; 530/300; 514/12

[56] References Cited

U.S. PATENT DOCUMENTS 5,468,624  11/1995  Thompson et al. ................ 435/69.1

OTHER PUBLICATIONS

Thompson, "Apoptosis and Steroid Hormones," *Molecular Endocrinology*, 8(6):665–673 (1994).

Thompson, "Lymphoid Cell Apoptosis by Glucocorticoids: The Roles of C–MYC Down–Regulation and Glucocorticoid Receptor Domains," *Clinical Endocrinology*, 43(5):535–545 (1995).

Giguère et al., "Functional Domains of the Human Glucocorticoid Receptor," *Cell*, 46:645–652, 1986, published in USA.

Harbour et al., "Steroid Mediated Lysis of Lymhoblasts Requires the DNA Binding Region of the Steroid Hormone Receptor," *J. Steroid Biochem.*, 35(1):1–9, 1990, published in USA.

Hollenberg et al., "Primary Structure and Expression of a Functional Human Glucocorticoid Receptor cDNA," *Nature*, 318:635–641, 1985, published in Europe.

Hollenberg et al., "Colocalization of DNA–Binding and Transcriptional Activation Functions in the Human Glucocorticoid Receptor," *Cell* 49:39–46, 1987, published in USA.

Nazareth et al., "Mapping the Human Glucocorticoid Receptor for Leukemic Cell Death," *J. Biol. Chem.*, 266(26):12976–12980, 1991, published in USA.

Thompson et al., "Glucocorticoids in Maligant Lymphoid Cells: Gene Regulation and the Minimum Receptor Fragment for Lysis," *J. Steroid Biochem. Molec. Biol.*, 41(3–8):273–282, 1992, published in Europe.

Nazareth et al., "Leukemic Cell Apoptosis Caused by Constitutively Active Mutant Glucocorticoid Receptor Fragments," *Recent Progress in Hormone Research, Proceedings of the 1993 Laurentian Hormone Conference*, 50:417–421, 1995.

*Primary Examiner*—Stephen G. Walsh
*Assistant Examiner*—Sally P. Teng
*Attorney, Agent, or Firm*—Arnold, White & Durkee

[57] ABSTRACT

A cell lysis factor which is a modified fragment of the human glucocorticoid receptor. The modified fragment designated 398–465*, when transfected into and expressed in a host cell, effects cell lysis and cell death. A pharmaceutical composition having the modified fragment 398–465* or the encoded protein product may be used in treatment of proliferative diseases.

2 Claims, 6 Drawing Sheets

% LYSIS
10⁻⁶M DEXAMETHASONE
-
6-24
HOURS
FOLLOWING TRANSFECTION
FIRST TRANSFECTION OF ICR 27 CELLS WITH 465*
465*  29
SECOND TRANSFECTION OF ICR 27 CELLS WITH 465* (48 HRS LATER)
465*  28
THIRD TRANSFECTION OF ICR 27 CELLS WITH 465* (96 HRS LATER)
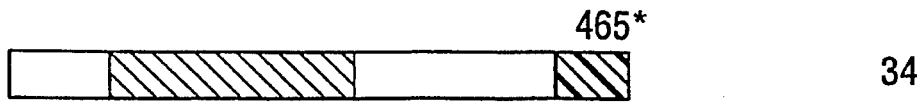
465*  34
FIG. 3

SEQ ID NO:1

BASE SEQUENCE OF MODIFIED FRAGMENT 398 - 465*

CCCGTTGGTTCCGAAAATTGGAATAGGTGCCAAGGATCTG

GAGATGACAACTTGACTTCTCTGGGGACTCTGAACTTCCC

TGGTCGAACAGTTTTTTCTAATGGCTATTCAAGCCCCAGC

ATGAGACCAGATGTAAGCTCTCCTCCATCCAGCTCCTCAA

CAGCAACAACAGGACCACCTCCCAAACTCTGCCTGGTGTG

CTCTGATGAAGCTTCAGGATGTCATTATGGAGTCTTAACT

TGTGGAAGCTGTAAAGTTTTCTTCAAAAGAGCAGTGGAAG

GACAGCACAATTACCTATGTGCTGGAAGGAATGATTGCAT

CATCGCGATAAAATTCGAAAAACTGCCCAGCATGCCGCT

ATCGAAAATGTCTTCAGGCTGGAATGA.

FIG.4

```
                                                    Modified GR    SEQ ID NO:2
                                                    Holo GR        SEQ ID NO:3

398
Met  Arg  Pro  Asp  Val  Ser  Ser  Pro  Ser  Ser  Ser  Ser
Met  Arg  Pro  Asp  Val  Ser  Ser  Pro  Ser  Ser  Ser  Ser

411
Thr  Ala  Thr  Thr  Gly  Pro  Pro  Pro  Lys  Leu  Cys  Leu  Val
Thr  Ala  Thr  Thr  Gly  Pro  Pro  Pro  Lys  Leu  Cys  Leu  Val

424
Cys  Ser  Asp  Glu  Ala  Ser  Gly  Cys  His  Tyr  Gly  Val  Leu
Cys  Ser  Asp  Glu  Ala  Ser  Gly  Cys  His  Tyr  Gly  Val  Leu

437
Thr  Cys  Gly  Ser  Cys  Lys  Val  Phe  Phe  Lys  Arg  Ala  Val
Thr  Cys  Gly  Ser  Cys  Lys  Val  Phe  Phe  Lys  Arg  Ala  Val

450
Glu  Gly  Gln  His  Asn  Tyr  Leu  Cys  Ala  Gly  Arg  Asn  Asp
Gly  Gly  Gln  His  Asn  Tyr  Leu  Cys  Ala  Gly  Arg  Asn  Asp 463         465   *
Cys  Ile  Ile  ala  ile  lys  phe  glu  glu  lys  thr  ala  gln
Cys  Ile  Ile  Asp  Lys  Ile  Arg  Arg  Lys  Asn  Cys  Pro  Ala his  ala  ala  ile  glu  asn  val  phe  arg  leu  glu  STOP
Cys  Arg  Tyr  Arg  Lys  Cys  Leu  Gln  Ala  Gly  Met............777
```

FIG.5

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 387 base pairs
( B ) TYPE: nucleic acid
( C ) STRANDEDNESS: double
( D ) TOPOLOGY: linear ( i i ) MOLECULE TYPE: genomic DNA ( x i ) SEQUENCE DESCRIPTION: SEQ ID NO:1:

```
CCCGTTGGTT   CCGAAAATTG   GAATAGGTGC   CAAGGATCTG   GAGATGACAA   CTTGACTTCT      60

CTGGGGACTC   TGAACTTCCC   TGGTCGAACA   GTTTTTTCTA   ATGGCTATTC   AAGCCCCAGC     120

ATGAGACCAG   ATGTAAGCTC   TCCTCCATCC   AGCTCCTCAA   CAGCAACAAC   AGGACCACCT     180

CCCAAACTCT   GCCTGGTGTG   CTCTGATGAA   GCTTCAGGAT   GTCATTATGG   AGTCTTAACT     240
```

```
TGTGGAAGCT GTAAAGTTTT CTTCAAAAGA GCAGTGGAAG GACAGCACAA TTACCTATGT    300

GCTGGAAGGA ATGATTGCAT CATCGCGATA AAATTCGAAA AAACTGCCCA GCATGCCGCT    360

ATCGAAAATG TCTTCAGGCT GGAATGA                                       387
```

( 2 ) INFORMATION FOR SEQ ID NO:2:

( i ) SEQUENCE CHARACTERISTICS:
        ( A ) LENGTH: 89 amino acid residues
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Arg Pro Asp Val Ser Ser Pro Pro Ser Ser Ser Ser Thr Ala Thr
 1               5                  10                  15

Thr Gly Pro Pro Pro Lys Leu Cys Leu Val Cys Ser Asp Glu Ala Ser
            20                  25                  30

Gly Cys His Tyr Gly Val Leu Thr Cys Gly Ser Cys Lys Val Phe Phe
        35                  40                  45

Lys Arg Ala Val Glu Gly Gln His Asn Tyr Leu Cys Ala Gly Arg Asn
    50                  55                  60

Asp Cys Ile Ile Ala Ile Lys Phe Glu Glu Lys Thr Ala Gln His Ala
65                  70                  75                  80

Ala Ile Glu Asn Val Phe Arg Leu Glu
                85
```

( 2 ) INFORMATION FOR SEQ ID NO:3:

( i ) SEQUENCE CHARACTERISTICS:
        ( A ) LENGTH: 89 amino acid residues
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met Arg Pro Asp Val Ser Ser Pro Pro Ser Ser Ser Ser Thr Ala Thr
 1               5                  10                  15

Thr Gly Pro Pro Pro Lys Leu Cys Leu Val Cys Ser Asp Glu Ala Ser
            20                  25                  30

Gly Cys His Tyr Gly Val Leu Thr Cys Gly Ser Cys Lys Val Phe Phe
        35                  40                  45

Lys Arg Ala Val Glu Gly Gln His Asn Tyr Leu Cys Ala Gly Arg Asn
    50                  55                  60

Asp Cys Ile Ile Asp Lys Ile Arg Arg Lys Asn Cys Pro Ala Cys Arg
65                  70                  75                  80

Tyr Arg Lys Cys Leu Gln Ala Gly Met
                85
```

MODIFIED POLYPEPTIDE FRAGMENTS OF THE GLUCOCORTICOID RECEPTOR

Research leading to the present invention was supported in part by U.S. Government grant NIH/NCI 5R01 CA41407. The U.S. government, therefore, has certain rights in the invention.

This is a divisional of application Ser. No. 08/087,151, filed Jul. 2, 1993, issued as U.S. Pat. No. 5,468,624 on Nov. 21, 1995.

BACKGROUND OF THE INVENTION

Glucocorticoids exert several effects in tissues which have receptors for them. They regulate the expression of several genes either positively or negatively and in a direct or indirect manner. They are also known to arrest the growth of certain lymphoid cells and in some cases cause cell death (1–5). Because of their ability to kill cells, glucocorticoids have been used for decades in the treatment of leukemias, lymphomas, breast cancer, solid tumors and other diseases involving irregular cell growth, e.g. psoriasis. The inclusion of glucocorticoids in chemotherapeutic regimens has contributed to a high rate of cure of certain leukemias and lymphomas which were formerly lethal (6). Although it is clear that glucocorticoids exert these effects after binding to their receptors, the mechanism of cell kill is not as yet understood although several hypotheses have been proposed. Among the more prominent hypotheses are: the deinduction of critical lymphokines, oncogenes and growth factors; the induction of supposed "lysis genes"; alterations in calcium ion influx; the induction of endonucleases and the induction of a cyclic AMP-dependent protein kinase (7–12).

The human glucocorticoid receptor is made up of 777 amino acids and is predominantly cytoplasmic in its unactivated, non-DNA binding form. When activated, it translocates to the nucleus. In order to understand the role played by the glucocorticoid receptor in the different cell processes, the receptor was mapped by transfecting receptor-negative and glucocorticoid-resistant cells with different steroid receptor constructs and reporter genes like CAT or luciferase which had been covalently linked to a glucocorticoid responsive element (GRE). From these studies, four major functional domains have become evident. From amino to carboxyl terminal end, these are: the tau 1, DNA binding, tau 2 and steroid binding domains in succession. The tau 1 domain spans amino acid positions 77–262 and regulates gene activation. The DNA binding domain is from amino acid positions 421–486 and has nine cysteine residues, eight of which are organized in the form of two zinc fingers analogous to Xenopus transcription factor IIIA. The DNA binding domain binds to the regulatory sequences of genes that are induced or deinduced by glucocorticoids. From amino acids 532–555 is the tau 2 domain which is the second domain important for transcriptional activation. Towards the carboxyl terminal end, from amino acids 555 to 777, is the steroid binding domain. This domain binds glucocorticoid to activate the receptor. This region of the receptor also has the nuclear localization signal. Deletion of this carboxyl terminal end results in a receptor that is constitutively active for gene induction (up to 30% of wild type activity) and even more active for cell kill (up to 150% of wild type activity) (13–26).

From previous experiments, the present inventors have shown that an intact GRE-specific DNA binding domain of the glucocorticoid receptor and its flanking sequences comprising in total, amino acids 1–8 connected to 386 through 532 is sufficient for the cell kill function of the receptor (27, 28). It was also shown that amino acids 1–465 were sufficient for the lethal function. Hollenberg et al. (14) describe constructs with $NH_2$ terminal deletions that lose activity for gene induction; and Dieken and Miesfeld (42) found that the amino terminal domain was required for cell kill. Thus the existing data indicated that at best some part of the amino terminal domain as well as the DNA binding domain were essential. A large additional body of published data has mapped many important functions of the receptor (nuclear translocation, heterologous protein-binding, ligand-binding, trans-activation) and thus its critical function required these domains (2–4, 18).

The present invention identifies a short sequence less than 100 amino acids in length, and not predicted from prior work, which is lethal in a cell line of T lineage. This sequence codes for only 23 amino acids preceding the DNA binding domain, and stops the domain short due to a missense mutation in the second zinc finger. The resulting predicted peptide replaces the normal carboxy-terminal end of the DNA binding domain with a missense sequence of 21 amino acids. Such a peptide could not be predicted, on the basis of published knowledge, to have any biological function and potency equal to that of holoreceptor plus steroid. Use of this construct in chemotherapeutic regimens could circumvent the need for steroid treatment in glucocorticoid-resistant malignant cells. When properly targeted towards a proliferative cell it may be used to cure several forms of proliferative disease.

ABBREVIATIONS dex: dexamethasone
GR: glucocorticoid receptor
GRE: glucocorticoid responsive element

SUMMARY OF THE INVENTION

The present invention provides for a cell lysis factor consisting essentially of the nucleotide sequence of SEQ ID NO:1. The nucleotide sequence may comprise biologically functional equivalents thereof. The invention also provides for a cell lysis factor consisting essentially of the amino acid sequence of SEQ ID NO:2. The amino acid sequence may also comprise biologically functional equivalents thereof.

A particular embodiment of the invention is a first polynucleotide purified free from total cellular DNA having the sequence of SEQ ID NO. 1, a second polynucleotide complementary to the first polynucleotide, a polynucleotide differing from the first or second polynucleotide by codon degeneracy, a polynucleotide which hybridizes with the first or second polynucleotide, or an oligonucleotide probe for the first or second polynucleotide which hybridizes with said polynucleotide.

A preferred embodiment of the invention is a polynucleotide encoding modified fragment 398–465* in substantially pure form defined as consisting essentially of the sequence of SEQ ID NO. 1 or biologically functional equivalents thereof.

A further embodiment of the invention is a recombinant nucleic acid molecule comprising a polynucleotide encoding modified fragment 398–465*. The recombinant molecule may be packaged for therapeutic delivery in a retroviral, adenoviral or other viral-based system. The recombinant nucleic acid molecule may be an expression vector for the overproduction of modified fragment 398–465*. A host cell comprising said expression vector is also an aspect of the invention.

The present invention is not limited to the particular nucleic acid and amino acid sequences of SEQ ID NO:1–2. DNA segments prepared in accordance with the present invention may also encode biologically functional equivalent proteins or peptides which have variant amino acid sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

The present invention also provides a method for treating an individual for a proliferative disease comprising the administration of a therapeutically effective amount of a modified fragment 398–465* which causes lysis of proliferating cells. The proliferating cells may be leukemia, myeloma, lymphoma, or other cancer cells; the modified fragment may have the sequence of SEQ ID NO. 1 and the administering may be parenteral or topical. The present invention also provides a method for treating an individual for a proliferative disease comprising the administration of a therapeutic effective amount of modified fragment peptide having SEQ ID NO. 2, either alone or "packaged" in any viral- or ligand-based delivery system.

In further related embodiments, the invention concerns processes for preparing compositions which include purified proteins or peptides with a sequence in accordance with SEQ ID NO:2. In a general sense, these processes include first selecting cells that are capable of expressing such a protein or peptide, culturing the cells under conditions effective to allow expression of the protein or peptide, and collecting the protein or peptide to thereby prepare the composition.

A particular embodiment of the present invention is a pharmaceutical composition comprising the cell lysis factors aforedescribed. The cell lysis factors may be packaged in a retroviral, adenoviral or other viral-based delivery system. The factors may be introduced into target cells by electroporation, conjugation to site-directed molecules or introduced by other means known to one skilled in the art.

A further embodiment of the present invention is a method of eliminating a selected cell population. The method comprises treating the cell population with a therapeutically effective amount of a modified fragment having the sequence of SEQ ID NO. 1, said sequence being under the control of an effective promoter sequence in an expression vector. The expression vector may be packaged in a viral delivery system having affinity for cell surface receptors of the selected cell population. The selected cell population may be a malignant cell population and the viral delivery system has affinity for cell surface receptors of the malignant cell population. The viral delivery system may have a proteinaceous coat which includes p120 of HIV-1, which is a ligand for the CD4 antigen found on the surface of certain normal and malignant lymphoid cells. The malignant cell population may be a leukemia, multiple myeloma, hepatoma or a lymphoma cell population. The cell surface receptor may be the asialoglycoprotein receptor.

A method of eliminating a selected cell population comprising treating the cell population with a therapeutically effective amount of a modified peptide fragment having the sequence of SEQ ID NO. 2 is a further embodiment of the present invention. In particular, the treatment is topical for dermatological applications and the peptide may form a mixture with lotions or creams that permit topical application.

BRIEF DESCRIPTION OF THE DRAWINGS

FIG. 3 demonstrates consistency of cell kill efficiency in ICR 27 cells. ICR 27 cells were transfected three times in succession allowing a 48 hour interval between successive electroporations, for recovery. The human GR and the constitutively lethal mutant construct 465* were used for the transfections. The holo GR served as a control to measure percentage cell lysis or reduction in viable cell number, in the absence (−) of dex following transfection. Values given represent maximum kill observed. Maximum kill with or without dex occurred between 6–24 hr. Each transfection was done in triplicate.

FIG. 4 shows the nucleotide sequence of the modified fragment of the present invention. The ATG at the beginning of line 4 is the first amino acid translated into a protein product. The last 63 nucleotides are frame-shifted from the wild-type sequence; the resultant encoded 21 amino acids are shown in lower case letters in FIG. 5.

FIG. 5 shows a comparison of the entire encoded amino acid sequence of the modified fragment of the present invention (top line) to the encoded amino acid sequence of the corresponding portion of the hologlucocorticoid receptor (lower line) from residue 398 to a position 21 amino acids carboxy-terminal to residue 465. The carboxy-terminal 21 amino acids in lower case letters of the modified fragment are the result of a frameshift mutation introduced by cloning. Those amino acids differ from that of the wild-type glucocorticoid receptor sequence.

DETAILED DESCRIPTION OF THE PREFERRED EMBODIMENTS

The present invention provides a modified fragment of the glucocorticoid receptor gene that, when transfected into cells, effects the lysis of those cells. This fragment, or equivalents thereof, may be used in a pharmaceutical composition for the treatment of proliferative diseases. Any proliferative cell, either glucocorticoid sensitive or resistant, could prove to be susceptible to lysis by the administration of this modified fragment.

Figure 1:
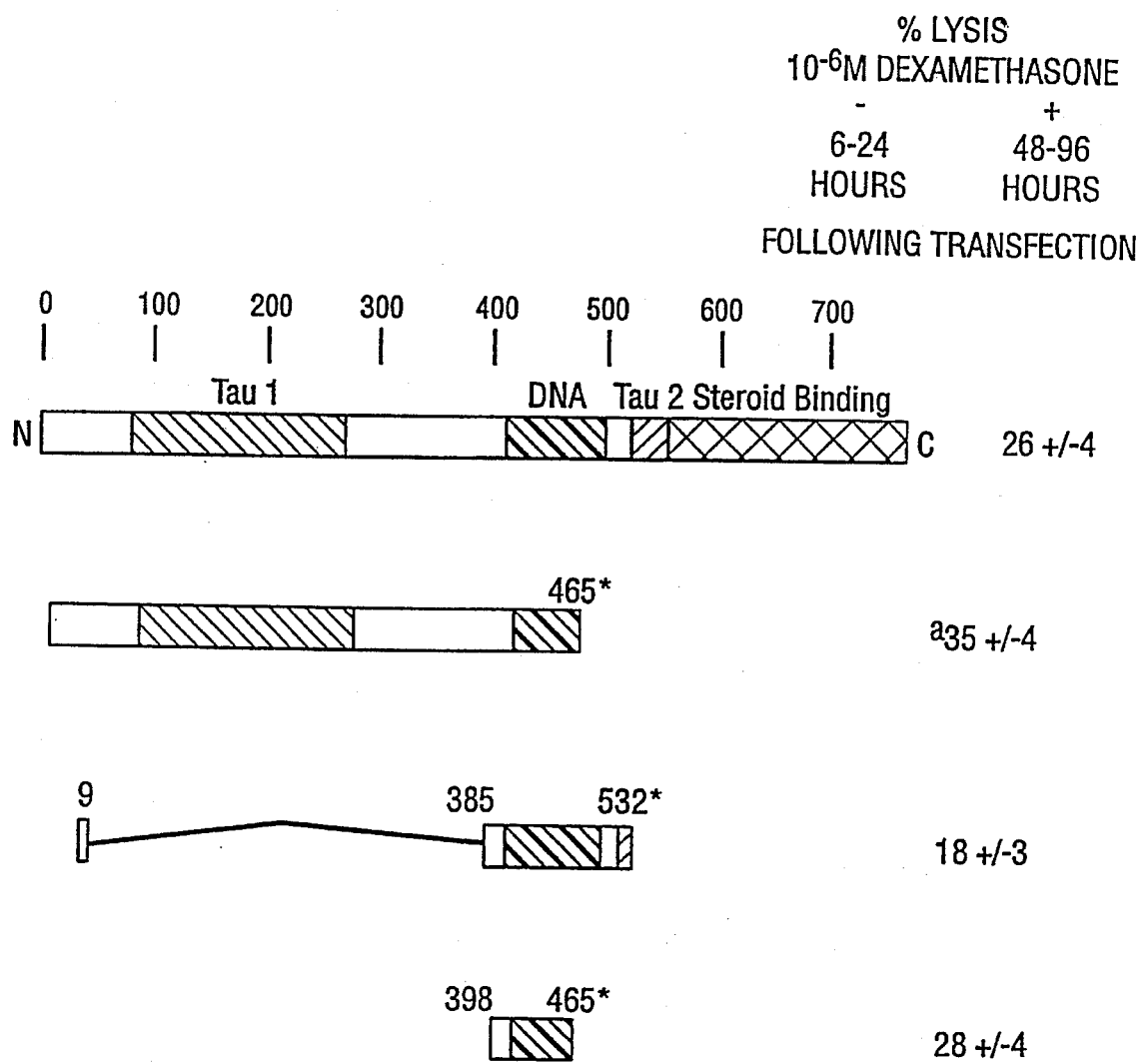
FIG. 1 shows the results of transfection of ICR 27 cells with GR constructs. ICR 27 cells were transfected with 4 different GR constructs, namely holo GR, 465*, Δ9-385/532* and the modified fragment 398–465* and followed for cell kill in the absence (−) or presence (+) of $10^{-6}$M dex for up to 96 hours after transfection. The numbers above the boxes correspond to the amino acid position in the protein sequence of the steroid receptor. The regions demarcated by the left diagonal hatches, the diamonds, the right diagonal hatches, and the chevrons correspond to the tau 1 domain, the DNA binding domain, the tau 2 domain, and the steroid binding domain, respectively. The percentage reduction in viable cell number, both in the absence (−) or presence (+) of dex, following transfection of ICR 27 cells with these steroid receptor constructs is indicated. Superscript "a" indicates results for cell kill that are significantly higher than that obtained for the holo GR plus dex, $p \leq 0.005$. Values given represent the averages of maximum kill observed in at least three transfections (each done in triplicate) along with standard deviations. A − sign indicates <4% cell lysis which is not considered significant. Maximum cell kill with the 398–465* fragment was seen at 6–24 hr and was the same in the presence or absence of dex.

In preliminary experiments, the present inventors mapped the major domains of the human glucocorticoid receptor for their role in leukemic cell death by transfecting glucocorticoid-resistant, glucocorticoid receptor-deficient cells with different glucocorticoid receptor mutant constructs. They found that the DNA binding domain was required. One active mutant contained the entire amino terminal domain through amino acid 465 of the DNA binding domain, followed by a predicted sequence of 21 missense amino acids. Another active mutant Δ9-385/532* lacked some of the amino terminal domain but contained the entire DNA binding domain. Data from Dieken and Miesfeld (42) suggested that undefined amino acids in the amino terminal domain of the glucocorticoid receptor are required for the lethal function. All other existing data with the exception of the present invention suggest that the entire 421-486 amino acid DNA binding domain is required for any function carried out by the glucocorticoid receptor. Thus, the present invention represents an unpredictable finding, since it defines a minimal and modified glucocorticoid receptor fragment capable of lethal action in the leukemia cells tested. The fragment lacks virtually all of the amino terminal domain up to the DNA binding domain as well as a complete DNA binding domain. It also contains a unique sequence of 21 amino acids beginning after the normal amino acid 465 of the human glucocorticoid receptor. The discovery that this small portion of the human glucocorticoid receptor (without added ligand) could be fully as active as hologlucocorticoid receptor (plus ligand) could not have been predicted from any published data. FIG. 1 shows a comparison of certain key constructs.

Tests of the efficacy of the modified fragment have included transient transfections. The efficiency of these transient assays was determined to be consistently in the range of 39%–51%, which is in agreement with the results of cell kill. Successive transfections of cells surviving transfection with glucocorticoid receptor constructs resulted in similar efficiencies of cell kill each time, confirming that electroporation was not merely eliminating sensitive subclones in the population but rather cells which took up the DNA. By blocking de novo protein and RNA synthesis, the onset of cell kill was arrested following transfection with an otherwise highly lethal constitutive receptor construct. Once the drug was removed and protein and RNA synthesis allowed to continue, the lysis cascade was reinitiated. These results indicate that the fragment or a gene under its control must be transcribed and/or translated into protein to function.

Figure 7:
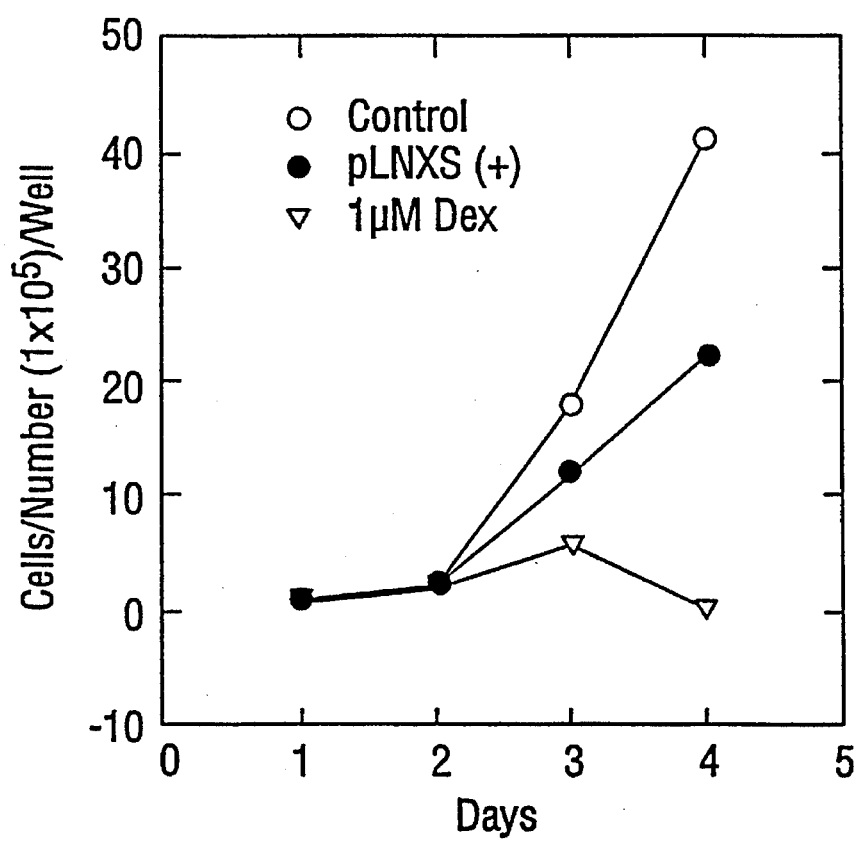
FIG. 7 shows a practicability study using a retroviral packaging system to deliver a constitutively lethal fragment of the GR gene to CEM-C7 cells. The GR construct 465* was placed in an expression plasmid under the control of the SV40 promotor. This was packaged in the amphitrophic GP and E86 system. Supernatant, virion-containing medium from the packaging cells was added directly to cultures of CEM-C7 cells (●). Control medium was added to the control cells with (▽) or without (o) 1 μM dexamethasone. Cultures were followed, with daily counts for viable cells, for 4 days.

A demonstration of the potential use of retroviral delivery systems for constructs similar to the modified fragment is provided in the experiment depicted in FIG. 7. These data show that a lethal construct of the GR, packaged and delivered in a retroviral system, can import its lethal function.

The 398–465* modified fragment of this invention has the sequence of nucleotides depicted in FIG. 4. An encoded protein would begin with a methionine (the ATG that begins line 4 of the sequence) which is amino acid 398 of the wild type glucocorticoid receptor (see FIG. 5 for the encoded amino acid sequence). At nucleotide 325 (nucleotide 1528 of the holoreceptor sequence) a frameshift mutation due to cloning results in the attachment of 21 amino acids unrelated to wild type glucocorticoid receptor. This construct is referred to as modified fragment. The 21 unrelated amino acids are in lower case letters in FIG. 5.

The 398–465* modified fragment of the present invention may contain a phosphorothioate substitution at each base to increase its resistance to in vivo hydrolysis (J. Org. Chem., 55:4693–4699, (1990) and Agrawal, (1990). The modified fragment or its phosphorothioate analogues may be synthesized using an Applied Biosystem 380B DNA synthesizer (Applied Biosystems, Inc., Foster City, Calif.). Peptides may be synthesized using an Applied Biosystems protein synthesizer.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Transfected "398–465*" into Glucocorticoid-Resistant CEM ICR27 Yields Constitutive Cell Kill Experimental Procedures
Preparation of Glucocorticoid Receptor Constructs The glucocorticoid receptor constructs pRShGRα, 465*, G424, G442, G455, G463 were kindly provided by Dr. S. M. Hollenberg (The Salk Institute, San Diego, Calif.) and were constructed as described (13,14). The construct termed 398–465* or modified fragment was constructed as described below. All the constructs are expression vectors under the control of the Rous sarcoma virus long terminal repeat and have the ampicillin resistance selection marker. The construct 465* is a carboxy terminal truncated mutant. Constructs G424, G442, G455 and G463 have glycine substitutions at conserved amino acid positions in the DNA binding domain. The modified glucocorticoid receptor fragment, namely 398–465*, was constructed using as the parent plasmid 465*. 465* DNA was linearized with BstXI which is a single cutter and generates a 5' overhang. The 5' overhang was blunt-ended with Klenow. KpnI linkers (8 mers) were ligated onto it and the DNA was cut with KpnI (which cuts the parental plasmid a single time and the linkers). The undesired DNA fragments (namely the 1.25 Kb smaller KpnI-BstXI fragment and linker pieces) were separated from the remaining sequence by agarose gel electrophoresis. The desired KpnI-BstXI fragment was religated to generate a circular plasmid which was named 398–465* (modified fragment). Amino acid number 398 is the first amino acid translated (methionine).

Fragments of the GR gene that served as negative controls for the transfections were: Δ420–451 (deletion of the first zinc finger); Δ450–487 (deletion of the second zinc finger); Δ428–490 (deletion of the entire DNA binding domain); I 422 (insertion of three amino acids between the first two cysteines in the first zinc finger); and GTG3A (chimeric GR having modified thyroid hormone receptor DNA binding domain which cannot recognize glucocorticoid response elements).

The plasmid DNA for the transfections was prepared by cesium chloride density gradients (29) or the pZ523 column chromatography purification procedure (5'→3' Inc., West Chester, Pa.) according to the manufacturer's instructions.

Cell Culture

ICR27 cells are a steroid-resistant subclone of CEM C7, human leukemic cells of T lineage. ICR 27 cells were grown in RPMI 1640 with 5% heat-inactivated fetal calf serum, pH 7.4, at 37° C. in incubators with humidified air and 5% carbon dioxide. Cells were maintained in the early to mid log phase by appropriate dilutions.

Transient Transfections

The transfections were performed as described (27). Cells in mid log phase were pelleted, washed three times with phosphate buffered saline devoid of $Ca^{++}$ and $Mg^{++}$ and resuspended to $4 \times 10^{-6}$ cells in 0.8 ml of saline. Fifteen μg of DNA was added and the mixture incubated on ice for 15 minutes prior to electroporating in gene pulser cuvettes, 0.4 $cm^2$ (BioRad Laboratories, Richmond, Calif.) at 200 V, 500 μF capacitance. The time constants or pulse time was recorded for each transfection—it ranged between 12 and 15 milliseconds. Five minutes after electroporating, the cells were resuspended to $4 \times 10^5$ cells/ml in RPMI 1640 with 5% serum and recultured. All the transfections were done in triplicate and repeated two or three times.

In experiments to verify the consistency of transfection efficiency, ICR 27 cells were electroporated three times in succession with glucocorticoid receptor constructs 465* and PRSHGRA. After each transfection, cell counts were determined soon after as well as 6, 12 and 24 hours after transfection. Cells were allowed to recover for 48 hours before being subject to a repeat pulse in the series of transfections.

Steroid Treatment

At 24 hours after transfection, cells were resuspended to $2 \times 10^5$ cells/ml in RPMI 1640 with 5% fetal bovine serum. When appropriate, dexamethasone (Sigma, St. Louis, Mo.) in ethanol was added to a final concentration of $10^{-6}$M. Ethanol vehicle was added to a final concentration of 0.1% to the control cells.

Cell Counts

Viable cell counts were determined by trypan blue exclusion as described (27). Cell counts and viability were determined immediately after electroporation, as well as 6, 12, 24, 48, 72 and 96 hours later. The cells in the flasks or plate wells were made monodisperse by triturating. Then a 0.1 ml aliquot of cells was added to 0.1 ml of 0.1% trypan blue (Gibco BRL, Gaithersburg, Md.) and mixed well. Immediately after, 15 μl of this mixture was added to the two chambers on either side of the hemocytometer so as to achieve even, random distribution of cells. Cell counts and viability (in terms of trypan blue exclusion) were determined at 100× magnification. All cells were scored as dye-positive (dead) or dye-negative (viable). At least 100 cells were counted for each sample. Initially, replicate aliquot fractions from each sample were counted to ensure the accuracy and precision of both sampling and counting. Such replicates varied no more than a few percent.

Determining the Efficiency of Transfection

In separate transfection experiments, ICR 27 cells were transfected by the protocol as described earlier with 15 μg of $P^{32}$-labeled DNA, specifically PRSHGRA, 465* and 398–465*. Each transfection was done in duplicate. To label the DNA, the plasmids were digested with KpnI (to generate a 3' overhang), incubated with T4 DNA polymerase (exonuclease reaction) for 5 minutes and then with the 4 deoxynucleotide triphosphates (the dCTP is $P^{32}$-labeled) for 30 minutes with excess cold dCTP added for an additional 15 minutes. This method of labeling generates plasmids whose ends are labeled ($10^7-2 \times 10^7$ DPM15/μg) and can be visualized by autoradiography. At 6 or 24 hours after electroporation, the cells were resuspended in 1 ml RPMI 1640 with 5% serum. One batch was treated with DNase I for 15 minutes to degrade any DNA sticking to the cell surface, and the other batch left untreated. The cells were then resuspended in 3.5–5.0 ml RPMI 1640 without serum and 50 μl and 100 μl of the cell suspension smeared per slide. The slides were air dried and coated with NTB2 emulsion (Eastman Kodak, Rochester, N.Y.), diluted 1:1 with deionized water. The slides were allowed to dry in the dark for approximately 2–3 hours. The slides were developed in two batches. The first batch was developed as early as 3 hours and the second 24–36 hours later in Kodak D19 developer for 3 minutes, rinsed in deionized water for 1 minute, fixed in Kodak fix for 5 minutes and washed two times in deionized water on ice for 5 minutes each. The slides were air dried and stained with Wright's stain for 7–10 minutes: then rinsed in deionized water to wash off the excess stain. Coverslips were mounted on the slides and the cells visualized at different magnifications ranging from 100× to 900×. The fraction of cells that had incorporated significant numbers of silver grains (above background i.e. ≧5 grains/cell) was recorded. Between 50–100 consecutive cells were counted per slide (4 slides per transfection).

Cycloheximide Treatment

Preliminary experiments were performed to determine the optimum concentration of cycloheximide to be used and the duration of treatment that would arrest protein synthesis but not kill cells. Initially, concentrations of cycloheximide in ethanol ranging from 0, 1, 5, 10 μg/ml were the effective concentrations tested. Ten μg/ml could effectively block protein synthesis but not kill cells. ICR 27 cells were treated with cycloheximide or ethanol vehicle before electroporation and subsequently to transfection with 465* and pRShGRα. Cell counts and viability were recorded 15 minutes after, as well as 6, 12 and 19 hours after electroporation. After 19 hours, the drug was washed out and viability recorded 15 minutes after as well as 6, 12 and 24 hours after the drug wash-out.

In follow-up experiments, doses of cycloheximide ranging from 0.1 μg/ml–1 μg/ml in ethanol were tested for their ability to block protein synthesis (in terms of inhibition of $S^{35}$-methionine uptake) preferentially over RNA synthesis (via inhibition of $H^3$-uridine uptake) at different times ranging from 30 minutes–8 hours incubation. One μg/ml of cycloheximide blocked protein synthesis to a greater extent than RNA synthesis after 4–6 hours incubation. ICR 27 cells were treated with cycloheximide or ethanol vehicle 30 minutes prior to electroporation. The cells were washed with PBS and transfected. Cycloheximide or ethanol was readded subsequent to transfection. At 30 minutes and 4–6 hours after transfection RNA and protein synthesis block was measured by incubating in the presence of the labeled precursors, TCA precipitating the products on glass fiber filters, and counting DPMs. Cell counts and viability were determined soon after electroporating as well as 6 hours after. After 6 hours the drug was washed out with PBS, and cell counts were determined 6 hours and 18 hours later.

Results and Discussion

Transfection of holo glucocorticoid receptor into glucocorticoid-resistant ICR 27 cells could restore cell lysis on addition of $10^{-6}$M dexamethasone (27,28,30). Since these were transient transfection assays, the extent of lysis was not 100%, but averaged 26±4% in 23 assays, each done in triplicate. The holoreceptor was used as a control in all transfections to compare the extent of cell lysis caused by receptor fragments. From previous mapping experiments, the present inventors determined that the amino terminal tau 1 domain and the carboxyl terminal tau 2 and steroid binding domains are dispensable for the cell lysis function. In fact, the present inventors have shown that construct Δ9-385/532* which encodes the central DNA binding domain and sequences flanking it on either side could effectively lyse cells in a constitutive manner (27,28). However no previous tests had been done proving that neither the carboxyl-terminal end of the DNA binding domain nor the amino acids 1-8 and 385–397 could be eliminated with full retention of the lethal function. In order to further delineate the minimal sequence encoding this function, the present inventors deleted progressively from either end towards the central DNA binding domain.

A "Modified Sequence" 398–465* of the Glucocorticoid Receptor Causes Cell Lysis

A modified fragment of the glucocorticoid receptor 398–465*, whose construction is described earlier, was used to transfect ICR 27 cells as shown in FIG. 1. Within 6–24 hours of transfection and in the absence of dexamethasone 28% of the cells were lysed—an extent comparable to that evoked by the holoreceptor and steroid 48–96 hours after transfection. Thus, a sequence which spans less than 100 amino acids is responsible for the constitutive lethality of the receptor. Although this property was seen in other constructs containing parts of the GR gene, it was unexpected and surprising to find full activity in the limited and altered sequence, 398–465*. The modified GR fragment lacks the entire amino terminal tau1 domain which is present in mutant 465* and also lacks the carboxyl terminal second half of the second zinc finger (present in mutant Δ9-385/532*) as well as the tau2 and steroid binding domains. 465* contains the entire amino terminal domain, and Dieken and Miesfeld's data (42) indicated that the amino terminal domain was essential for lethal activity. The present inventors previous data with partial deletions of the amino terminal domain of the GR always included parts of that region and the entire DNA binding domain. That a sequence containing a DNA binding domain mutated in its 3' portion, and only the 22 proximal amino acids at the amino terminal end would be fully active was both unexpected and surprising (FIG. 1).

The following fragments or mutations of the GR gene were inactive for cell lysis upon transfection: Δ420–451 (deletion of the first zinc finger); Δ450–487 (deletion of the second zinc finger); Δ428–490 (deletion of the entire DNA binding domain); I 422 (insertion of three amino acids between the first two cysteines in the first zinc finger); and GTG3A (chimeric GR having modified thyroid hormone receptor DNA binding domain which cannot recognize glucocorticoid response elements). Four point mutants having glycine substitutions in key amino acid positions in the zinc finger structure of the DNA binding domain were selected to test their importance in the cell kill process. The constructs transfected were G424, G442, G455 and G463—all glycine substitutions (see Table 1). (14)

TABLE 1

EFFECTS OF TRANSFECTED GR POINT MUTANTS

| Gly Substitution | | GRE Binding[a] | Percent Wild Type GR Induces MMTV-CAT[a] | Represses α-subCG[b] | Cell Kill in ICR 27[c] |
|---|---|---|---|---|---|
| Aa # | (n = 6) | | | | |
| 424 | Cys2 Zn finger1 | 1 | <1 | <10 | Inactive |
| 442 | Conserved lys knuckle | 60 | <1 | 68 | Inactive |
| 455 | Conserved tyr inter finger | 6 | 80 | Not det. | Inactive |
| 463 | Cys2 Zn finger2 | 1 | <1 | <10 | Inactive |

[a]Hollenberg, S.M. et al., (1988) Cell 55:899
[b]Oro, A.E. et al., (1988) Cell 55:1109
[c]Four mutants having single glycine substitutions in the DNA binding domain of the GR were transfected into ICR 27 cells. The four constructs were G424, G442, G455, and G463. Indicated in the table are some of the properties of the constructs as determined by other investigators as well as results for cell kill. GRE binding is measured in terms of the ability of these mutants to bind to a GRE-cellulose column. The ability of these constructs to induce MMTV-CAT and repress the α-subunit of chorionic gonadotropin is shown. A figure of 100 in any of these columns would indicate binding, activation or repression equivalent to that of the wild type. ICR 27 cells were transfected with these constructs and followed for cell kill in terms of reduction in viable cell number, in the absence or presence of dex. Inactivity for cell kill represents <4% cell lysis, as compared to wild type (equivalent to 26% as indicated earlier in FIG. 1).

The construct G424 replaces the second cysteine in the first zinc finger thereby disrupting the finger. Construct G442 replaces the conserved lysine at the base of the first zinc finger (in the knuckle region). An interesting aspect of this construct is that it had been shown to bind GREs but was unable to activate MMTV-CAT. Construct G455 substitutes a conserved tyrosine in the linker region separating the two zinc fingers. This construct was also interesting because it had been shown to bind GREs very weakly but yet could effectively stimulate transcription of MMTV-CAT. Construct G463 alters the second cysteine in the second zinc finger thereby disrupting the finger. All the mutants were transfected into ICR 27 cells followed for kill in the presence/absence of $10^{-6}$M dexamethasone. All of them proved to be inactive for cell kill, stressing their importance in glucocorticoid receptor-mediated apoptosis.

Effect of Transfections on Hematopoietic Cell Lines

TABLE 2

LETHAL EFFECTS OF 465* & GR
ON HEMATOPOIETIC CELL LINES

| | MAXIMUM PERCENT KILL | | |
|---|---|---|---|
| | INHERENT RESPONSE | TRANSFECTED RESPONSE | |
| 465* | – | + | – |
| GR | – | – | + |
| 1 µM Dex | + | – | + |
| CELL TYPE | | | |
| Lymphoid T | | | |
| ICR 27 | 4 | 35 +/– 4 | 26 +/– 4 |
| MOLT 4 | 4 | 33 +/– 3 | 25 +/– 3 |
| JURKAT | <1 | 24 +/– 5 | 29 +/– 2 |
| Lymphoid B | | | |
| IM9 | 2 | 32 +/– 1 | 30 +/– 1 |
| RPMI 8226 | 10 | 28 +/– 3 | 28 +/– 0.5 |
| Myeloid and B | | | |
| HL 60 (Myeloid) | <1 | 0 | 0 |
| TMM (Myeloid and B) | 2 | 0 | 0 | n = 3–6

Table 2 indicates the maximum percentage cell kill along with standard deviation values, seen in different cell lines, either after transfection with GR constructs 465* without 1 µM dex (in the second column) or the entire GR in the presence of 1 µM dex (in the third column). Also indicated (in the first column) is the inherent sensitivity of these cell lines to 1 µM dex. Note that all these cell lines are relatively dex-insensitive. The results in the table are obtained from 3–6 transfections (n).

Efficiency of Transient Transfections Correlates with Quantity of Cell Kill

Figure 2A:
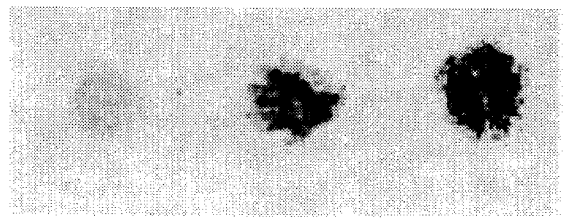
FIG. 2 shows the uptake of labeled plasmid in transient transfections with glucocorticoid receptor constructs in ICR 27, HL-60 and TMM cells. The efficiency of transient transfections was calculated in terms of the fraction of cells that had incorporated $P^{32}$-labeled DNA during electroporation. The three panels A, B and C correspond to three cell lines ICR 27, HL-60 and TMM respectively. The silver grains in the cells represent labeled DNA visualized through an autoradiographic emulsion. Represented in panel A are three individual ICR 27 cells. The leftmost cell is a typical example of an untransfected cell; in the middle is a cell that has incorporated moderate amounts of label and to the right is a heavily labeled cell. In panel B are two HL-60 cells. On the left is an example of an untransfected cell whereas on the right is an example of a transfected cell. Panel C corresponds to the TMM cells. On the left is a cell that is not transfected and on the right is a transfected cell. For all three cell lines, efficiency of transfection was about 40%.
Figure 2B:
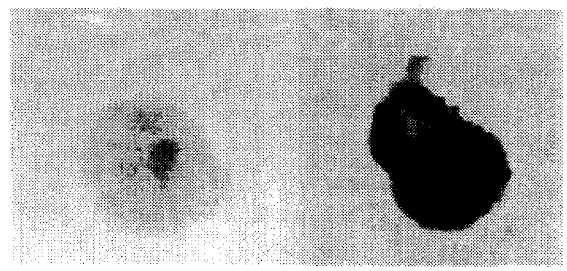
Figure 2C:
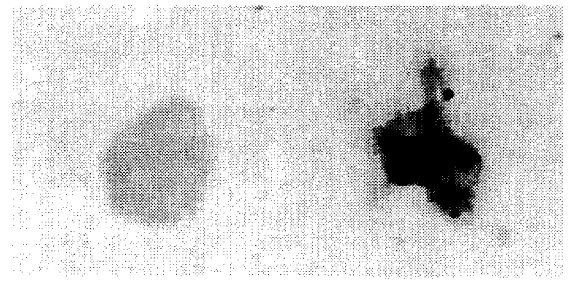
Figure 6:
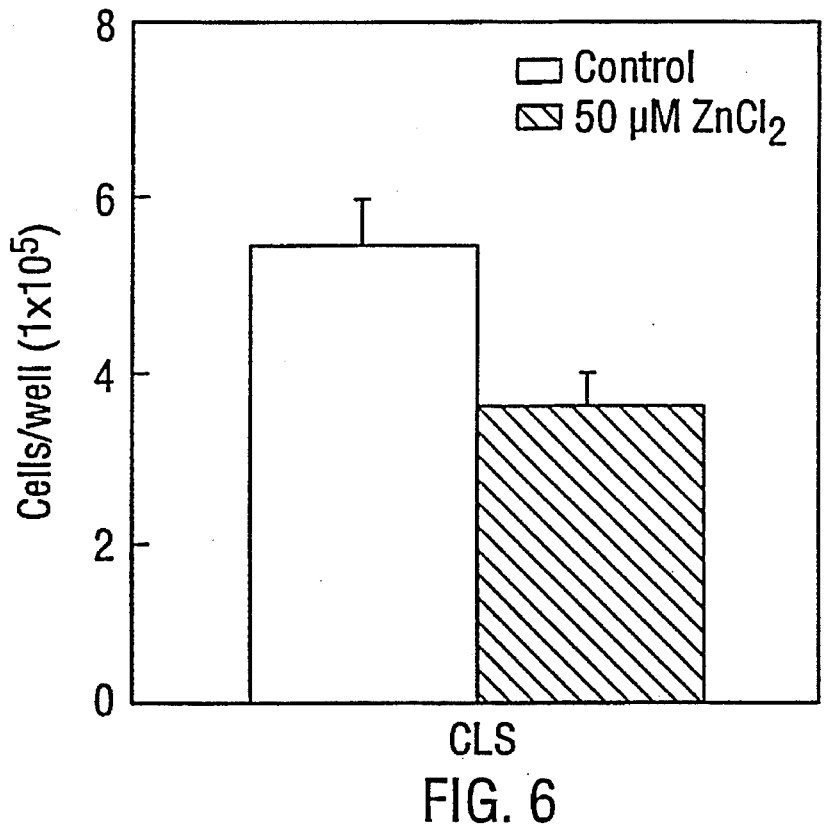
FIG. 6 shows that 465* is made an endogenous cellular gene, its induction kills dex-resistant CEM cells. Stably transfected colony CLS contains the 465* mutant GR under the control of the $Zn^{++}$-inducible MT promoter. Equal initial numbers of CLS cells were treated with vehicle only (open bar) or 50 μM $ZnCl_2$ (hatched bar) for 24 hr. The cultures were then counted for viable cells. Error bars=1 standard deviation. N=3.

The efficiency of transfection was determined in several experiments as all the assays were transient and no reporter gene had been co-transfected to serve as a control. ICR 27 cells were transfected with $P^{32}$-labeled constructs pRShGRα, 465* and 398–465* in two separate transfection experiments. The labeled DNA in the cells was visualized by autoradiography. In the transfections with the holoreceptor between 40%–50% of the cells were labeled, for transfections with 465* and 398–465* between 39%–50% and 40%–51% of the cells respectively had label (FIG. 2). The extent of label varied from transfected cell to transfected cell. All cells were scored as labeled if they had 5 or more grains (5 considered background or unlabeled). The results of cell kill varied between 22%–39% (27) for these three glucocorticoid receptor constructs, which correlates well with the results of transfection efficiency, since it would be expected that a proportion of cells transfected would retain and express sufficient DNA to show the lethal effect.

Response to Transient Transfections of ICR 27 Cells with Glucocorticoid Receptor Is Not Occurring Only in Sensitive Subclones To determine if similar fractions of cells would be killed if the cells surviving transfection are electroporated repeatedly, ICR 27 cells were electroporated three times in succession with 465* or the holoreceptor (as a control) as shown in FIG. 3. After each transfection, cells were allowed to recover for 48 hours before being subjected to a repeat pulse. Similar fractions of cells were killed each time between 6–24 hours after electroporation with 465*. viz. 29%, 28% and 34%.

De Novo RNA and/or Protein Synthesis Is Required for Glucocorticoid Receptor Mediated Cell Kill Cycloheximide was used to block de novo protein synthesis and/or RNA synthesis to determine if the lethal effects of 465* were specifically due to a product of transfection rather than transfection of the DNA itself into cells. The cell lethality kinetics of 465* are quick and therefore compatible with the maximum possible duration of non-toxic cycloheximide treatment. In 10 µg/ml cycloheximide, ICR 27 cells survive for up to 21 hours with both RNA and protein synthesis blocked. This treatment prevents the onset of kill by transfected 465*. After the drug is removed, cell kill proceeds with the usual 6–24 hr kinetics (Table 3). Therefore de novo RNA and/or protein synthesis are/is required.

TABLE 3

THE EFFECTS OF CYCLOHEXIMIDE (10 µg/ml)
ON LYSIS IN TRANSFECTED ICR 27 CELLS[1]

| Time: (Hrs) | –2 | 0 | 18 | 24 | 48 |
|---|---|---|---|---|---|
| | Cyclohex treatment | Transfect with 465* | Wash out cyclohex | | Cell Kill Observed |
| | |_____| |_____| |
| | | No Cell Kill Observed | | | |
| Time: (Hrs) | | 0 | 6 | 24 | |

TABLE 3-continued

THE EFFECTS OF CYCLOHEXIMIDE (10 µg/ml) ON LYSIS IN TRANSFECTED ICR 27 CELLS[1]

Transfect      Cell Kill
with 465°     Observed

|————————|

% CELL KILL

| 10 µg/ml Cyclohex | | After wash-out |
|---|---|---|
| − | + | +/− |
| 6–24 HOURS | 6–24 HOURS | 6–24 HOURS |
| 27 +/−3 | 3 +/−0.5 | 31 +/−6.5 |

[1] - The table has linear scales of the time course of events occurring during and after cycloheximide treatment and wash-out in ICR 27 cells that have been transfected with GR construct 465*. The holo GR serves as a control. Represented are two time scales. The one in the top half represents treatment of transfected ICR 27 cells with cycloheximide from −2 to 18 hours (−2 representing 2 hours prior to transfection and 18 representing 18 hours after transfection). At 18 hours, cycloheximide is washed out and cell kill is observed between 24 (18 + 6) hours and 48 (18 + 30) hours after transfection. The time scale in the lower half represents the control population of transfected cells which had been treated with ethanol vehicle from 0 to 24 hours. Cell kill, here, is observed between 6 and 24 hours after transfection. Represented in the lowermost portion is the extent of cell lysis with respect to ICR 27 controls which had been transfected with holo GR. The percentage cell lysis is indicated in the absence (−) and presence (+) of 10 µg/ml cycloheximide as well as after wash-out of cycloheximide (+/−).

One µg/ml of cycloheximide is a dose that would block protein synthesis to a greater extent (69%) than RNA synthesis (35%) after 4–6 hours of treatment (Table 4). Therefore, the experiment was repeated under block at this dose, with the same results. These data suggest more strongly that protein synthesis as well as RNA synthesis is required for the lethal effect (Table 4).

TABLE 4

THE EFFECT OF CYCLOHEXIMIDE (1 µg/ml) ON RNA AND PROTEIN SYNTHESIS AND LYSIS IN TRANSFECTED ICR 27 CELLS[1]

| Time: (Hrs) | −0.5 | 0 | 6 | 12 | 24 |
|---|---|---|---|---|---|
| | Cyclohex treatment | Transfect with 465* | Wash out cyclohex | | Cell Kill Observed |

|————————|    |————————|

No Cell Kill Observed

| Time: (Hrs) | 0 | 6 | | 24 |
|---|---|---|---|---|
| | Transfect with 465* | | | Cell Kill Observed |

|————————————————|

% INHIBITION:RNA SYNTHESIS 36%
PROTEIN SYNTHESIS 69% AFTER 6 HOURS CYCLOHEX
% CELL KILL

| 1 µg/ml Cyclohex | | After wash-out |
|---|---|---|
| − | + | +/− |
| 6 HOURS | 6 HOURS | 6–18 HOURS |
| 25 | 4 | 25 |

TABLE 4-continued

THE EFFECT OF CYCLOHEXIMIDE (1 µg/ml) ON RNA AND
PROTEIN SYNTHESIS AND LYSIS IN TRANSFECTED ICR 27 CELLS[1]

[1] - The table has linear scales of the time course of events occurring during and after cycloheximide treatment and wash-out in ICR 27 cells that have been transfected with GR construct 465*. The holo GR serves as a control. Represented are two time scales. The one in the top half represents treatment of transfected ICR 27 cells with cycloheximide from −0.5 to 6 hours (−0.5 representing 30 minutes prior to transfection and 6 representing 6 hours after transfection). At 6 hours, cycloheximide is washed out and cell kill is observed between 12 (6 + 6) hours and 24 (6 + 18) hours after transfection. The time scale in the lower half represents the control population of transfected cells which had been treated with ethanol vehicle from 0 to 24 hours. Cell kill, here, is observed between 6 and 24 hours after transfection.
Represented in the lowermost portion is the extent of cell lysis and inhibition of RNA and protein synthesis with respect to ICR 27 controls which had been transfected with holo GR. The percentage cell lysis is indicated in the absence (−) and presence (+) of 1 µg/ml cycloheximide as well as after wash-out of cycloheximide (+/−). The percentage inhibition of RNA and protein synthesis is indicated as a percentage of control.

The modified lethal fragment of the receptor, 398–465*, starts 23 amino acids upstream from the DNA binding domain, goes through the first zinc finger, the linker region which follows it and through amino acid position 465 in the second zinc finger. It then switches to 21 missense amino acids and stops. It has some sequence important for binding GREs but lacks signals for transcriptional activation, nuclear localization, steroid binding, and most sites for protein:protein interactions. It is constitutively active and can kill cells in which it is expressed within 6–24 hours of transfection. The construct is as effective in effecting cell lysis as is the holoreceptor in the presence of steroid. Several of the conserved amino acids within this modified fragment are highly important for the lethality of this construct. The first 4 cysteine residues are important, since they form the backbone of the first zinc finger structure which binds the GREs in regulated genes. The mutants which had single amino acid substitutions in the DNA binding domain were functionally inactive for cell kill, stressing the importance of an intact DNA binding domain (at least halfway through the second zinc finger).

The efficiency of transient transfection assays was consistently in the range of 39%–51% irrespective of the gene construct used. These values are slightly higher than the values seen for cell kill which ranged between 22%–39% for the three constructs pRShGRα, 465* and 398–465* tested. This difference could be explained by presuming that a certain minimum threshold level of the glucocorticoid receptor protein would have to be expressed in order to kill the cells.

By repeatedly transfecting cells surviving transfection (three times in succession) similar killing efficiency was obtained and rules out the possibility that the transfections were wiping out more sensitive cells in a population rather than randomly killing cells which took up the DNA and expressed it.

Cell kill requires the de novo synthesis of one or more specific RNAs and proteins and is not an effect of DNA toxicity on the cell. In fact, Harbour et al. have shown that after transfecting ICR 27 cells with pRShGRα, there is an increase in the number of dexamethasone binding sites to 3,600 from 1,000 (30). This increases the receptor number to within the order of magnitude of wild-type levels and is not an over-expression of protein. Although the mechanism of glucocorticoid receptor-mediated cell death is not fully understood, several candidate genes have been selected as potential lysis cascade candidates. Among them may be genes that are important in cellular proliferation: c-myc (9, 36, 37), the oncogenes los and jun which bind at the AP1 site (38, 39), as well as endonucleases like NUC 18 which has been identified by Cidlowski to cause nuclear fragmentation (40).

This modified gene fragment construct provides a new approach to chemotherapeutic regimens, by killing malignant cells, including but not limited to those resistant to steroid treatment. The construct could also be used for therapy against certain components of the immune system in diseases of immune-hyperactivity, or for other instances in which tissue hypertrophy is known to respond to treatment with glucocorticoids, e.g., psoriasis.

EXAMPLE 2

Delivery System for Therapeutic Use of Modified Fragment 398–465*

The present inventors have achieved "packaging" of the sequence carrying amino acids 1–465*, including the novel extension, into an amphitropic retrovirus. The titer achieved was low, but the recombinant virus showed significant cell kill compared to controls.

FIG. 6 shows that induction of endogenous cellular 465* kills dex-resistant CEM cells. Stably transfected clone CLS contains the 465* mutant GR under the control of the $Zn^{++}$-inducible MT promoter. Equal initial numbers of CLS cells were treated with vehicle only (open bar) or 50 μM $ZnCl_2$ (hatched bar) for 24 hr. The cultures were then counted for viable cells.

The GR construct 465* was also placed in an expression plasmid under the control of the SV40 promoter. This was packaged in the amphitrophic GP and E 86 system. Supernatant medium from the packaging cells was collected and added directly to cultures of CEM-C7 cells. This medium should contain the expression vector packaged in the amphitrophic viral coat. Cultures were followed for 4 days, with cell counts daily. The data (FIG. 7) show that despite the low titers, there was significant kill. This demonstrates the feasibility of this or other viral systems for delivery of such constructs. The same system will be used for the delivery of the modified fragment 398–465*. Alternative vectors for delivery include adenovirus or a deactivated human immunodeficiency virus.

Cell surface receptors may be exploited for the delivery of the modified fragment. For example, the asialoglycoprotein receptor has been used to carry DNA into liver cells. The DNA is attached to a ligand, in particular to a galactose residue, which is specifically bound by the receptor. Liver cells and lymphoid cells are particularly rich in this receptor. Various hematopoietic cell receptors, e.g. CD4, may be used to deliver the modified fragment to specific sites. The ligand for the CD4 receptor, p120, may be attached to the modified fragment for uptake into lymphocytes.

The modified fragment may be small enough to be taken up directly by cells. Phosphorothioate derivatives of nucleotides may be used in the synthesis of the DNA so as to protect the modified fragment from degradation as has been demonstrated (Cancer Res. 51:3996, 1991). The modified fragment may be also be encapsulated into liposomes for delivery to targeted cells.

The following references are incorporated in pertinent part by reference herein for the reasons cited above.

REFERENCES

1. Harmon et al., (1979), *J. Cell Physiol.* 98:267–278.
2. Yamamoto, K. R. (1985), *Ann. Rev. Genet.* 19:209–252.
3. Evans, R. M. (1988), *Science* 240:889–895.
4. Beato, M. (1989), *Cell* 56:335–344.
5. Thompson, E. A. (1989), *Cancer Res.* 49:2259s–2265s.
6. Homo-Delarche, F. (1984), *Cancer Res.* 44:431–437.
7. McConkey et al. (1989), *Arch. Biochem. Biophys.* 269:365–370.
8. Cohen, J. C. and Duke, R. C. (1984), *J. Immunol.* 152:38–42.
9. Eastman-Reks, S. B. and Vedeckis, W. V. (1986), *Cancer Res.* 46:2457–2462.
10. Kelso, A. and Munck, A. (1984), *J. Immunol.* 133:784–791.
11. Gruol et al. (1989), *Molec. Endocrinol.* 3:2119–2127.
12. Yuh, Y-S. and Thompson, E. B. (1989), *J. Biol. Chem.* 264:10904–10910.
13. Giguere et al. (1986), *Cell* 46:645–652.
14. Hollenberg et al. (1987), *Cell* 49:39–46.
15. Hollenberg, S. M. and Evans, R. M. (1988), *Cell* 55:899–906.
16. Hollenberg et al. (1989), *Cancer Res.* 49:2292s–2294s.
17. Oro et al. (1988), *Cell* 55:1109–1114.
18. Evans, R. M. (1989), In: *Recent Progress in Hormone Research* (Clark, J. H., ed.) Vol. 45, pp. 1–27, Academic Press, San Diego, Calif.
19. Green, S. and Chambon, P. (1987), *Nature* 325:75–78.
20. Picard, D. and Yamamoto, K. R. (1987), *EMBO J.* 6:3333–3340.
21. Picard et al. (1990), *Cell Regulation* 1:291–299.
22. Godowski et al., (1987), *Nature* 325:365–368.
23. Miesfeld et al., (1987), *Science* 236:423–427.
24. Danielsen et al., (1989), *Cancer Res.* 49:2286s–2291s.
25. Danielsen et al., (1987), *Molec. Endocrinol.* 1:816–822.
26. Umesono, K. and Evans, R. M. (1989), *Cell* 57:1139–1146.
27. Nazareth et al., (1991), *J. Biol. Chem.* 266:12976–12980.
28. Thompson et al., (1992), *J. Steroid Biochem. Molec. Biol.* 41:273–282.
29. Maniatis et al., (1982), In: *Molecular Cloning: A Laboratory Manual,* (Maniatis, T., Fritsch, E. F., and Sambrook, J., ed) pp. 88–96. Cold Spring Harbor Laboratory, New York.
30. Harbour et al., (1990), *J. Steroid Biochem.* 35:1–9.
31. Wyllie, A. H. (1980), *Nature* 284:555–556.
32. Cohen, J. J. (1991), *Advances Immunol.* 50:55–85.
33. Mader et al., (1989), *Nature* 338:271–274.
34. Danielsen et al., (1989), *Cell* 57:1131–1138.
35. Green et al., (1988), *EMBO J.* 7:3037–3044.
36. Forsthoefel, A. M. and Thompson, E. A. (1987), *Mol. Endocrinol* 1:899–907.
37. Thompson et al., (1989), In: *The Steroid/Thyroid Hormone Receptor Family and Gene Regulation* (Gustafsson, J. A., Eriksson, H., and Carlstedt-Duke, J., ed), pp. 127–145, Birkhauser-Verlag, Basel.
38. Schule et al., (1990), *Cell* 62:1217–1226.
39. Lucibello et al. (1990), *EMBO J.* 9:2827–2834.
40. Gaido, M. L. and Cidlowski, J. A. (1991), *J. Biol. Chem.* 266:18580–18585.
41. Owens et al. (1991), *Molec. Cell. Biol.* 11:4177–4188.
42. Dieken and Miesfeld (1992), *Molec. Cell. Biol.* 12:589.

It is understood that the examples and embodiments described herein are for illustrative purposes only and that various modifications in light thereof will be suggested to persons skilled in the art and are to be included within the spirit and purview of this application and scope of the appended claims.

---

What is claimed is:

1. A cell lysis factor consisting of the amino acid sequence of SEQ ID NO:2.

2. A pharmaceutical composition comprising the cell lysis factor of claim 1 and a pharmaceutically acceptable carrier.

* * * * *